(12) United States Patent
Noori

(10) Patent No.: US 8,779,385 B2
(45) Date of Patent: Jul. 15, 2014

(54) METHOD AND DEVICE FOR ULTRAVIOLET LIGHT STERILIZING

(76) Inventor: Gilda Noori, Los Angeles, CA (US)

( * ) Notice: Subject to any disclaimer, the term of this patent is extended or adjusted under 35 U.S.C. 154(b) by 421 days.

(21) Appl. No.: 13/089,092

(22) Filed: Apr. 18, 2011

(65) Prior Publication Data
US 2012/0261593 A1 Oct. 18, 2012

(51) Int. Cl.
*B01J 19/12* (2006.01)
*B01J 19/08* (2006.01)

(52) U.S. Cl.
USPC ............. 250/455.11; 250/461.1; 250/504 R; 422/24; 422/124; 422/186.3

(58) Field of Classification Search
USPC ......... 250/455.11, 461.1, 438, 504 R, 504 H; 42/24, 120, 121, 186.3; 422/24, 50, 422/120, 121, 186.3
See application file for complete search history.

(56) References Cited

U.S. PATENT DOCUMENTS

| | | | | |
|---|---|---|---|---|
| 6,090,346 A * | 7/2000 | Rose et al. | | 422/20 |
| 6,171,548 B1 * | 1/2001 | Rose et al. | | 422/20 |
| 6,468,419 B1 * | 10/2002 | Kunkel | | 210/90 |
| 6,576,188 B1 * | 6/2003 | Rose et al. | | 422/20 |
| 6,984,259 B2 * | 1/2006 | Hurst | | 95/273 |
| 7,560,706 B1 * | 7/2009 | Castelluccio | | 250/455.11 |
| 7,875,247 B2 * | 1/2011 | Clark et al. | | 422/121 |
| 7,888,657 B1 * | 2/2011 | Zadro | | 250/455.11 |
| 7,931,859 B2 * | 4/2011 | Mlodzinski et al. | | 422/24 |
| 8,084,752 B2 * | 12/2011 | Ranta et al. | | 250/455.11 |
| 8,168,963 B2 * | 5/2012 | Ratcliffe | | 250/504 H |
| 8,182,744 B2 * | 5/2012 | Mlodzinski et al. | | 422/50 |
| 8,404,186 B2 * | 3/2013 | Clark et al. | | 422/120 |
| 2002/0168287 A1 * | 11/2002 | Eckhardt et al. | | 422/24 |
| 2008/0152548 A1 * | 6/2008 | Clark et al. | | 422/121 |
| 2008/0199353 A1 * | 8/2008 | Mlodzinski et al. | | 422/24 |
| 2008/0286145 A1 * | 11/2008 | Ratcliffe | | 422/24 |
| 2009/0218512 A1 * | 9/2009 | Ranta et al. | | 250/455.11 |
| 2011/0139999 A1 * | 6/2011 | Clark et al. | | 250/438 |
| 2011/0172810 A1 * | 7/2011 | Mlodzinski et al. | | 700/230 |
| 2013/0256560 A1 * | 10/2013 | Yerby | | 250/455.11 |

* cited by examiner

*Primary Examiner* — Bernard E Souw
(74) *Attorney, Agent, or Firm* — Adli Law Group P.C.

(57) ABSTRACT

In accordance with the present invention, a device and method is provided for covering and sterilizing a stethoscope or other medical instrument for safer use. The device comprises a closed housing for shielding the object to be sterilized, a means for receiving the object, a power supply, an ultraviolet light source within the housing, and a switch for controlling that lamp.

13 Claims, 4 Drawing Sheets

METHOD AND DEVICE FOR ULTRAVIOLET LIGHT STERILIZING

BACKGROUND OF THE INVENTION

This invention relates to a method and device employing ultraviolet light to sterilize medical instruments.

One common problem that hospitals face today is the spread of nosocomial infections. Many of these infections are caused by organisms that have become resistant to the anti-microbial arsenal. The nosocomial infections pose a huge health and financial burden on hospitals, doctors, and patients. People infected by these resistant organisms often have to be hospitalized for extended periods of time and pay for expensive anti-microbial medications. Furthermore, a significant percentage of infected patients are prone to ultimate health deterioration and potentially fatal consequences.

Nosocomial infections are frequently caused by medical staff that inadvertently spread disease from one patient to another. Poor hand washing, re-use of medical devices, or failure to sterilize the environment, all may increase the chance of distributing the microbial organisms. However, with hand washing becoming widely practiced in hospitals, medical devices are now a main channel to the spread nosocomial infections. By way of example, stethoscopes are a very common medical device that is used recurrently on different patients wherein the medical worker brings the head of the stethoscope, which contains the bell or diaphragm, into contact with the patient's body. They act as a vector to spread microorganisms and diseases. Therefore, patients in isolation are often treated using a "disposable" stethoscope, which can provide only limited patient information due to its inferior quality.

As most resistant microbes are vulnerable to the germicidal effects of the UV radiation, the ultraviolet (UV) light technology is commonly used to sterilize surfaces. The UV light source, as implemented in conventional techniques, is typically placed in a housing constructed of materials such as glass or clear plastic. The housing has been adapted to fit in a shirt or jacket pocket of a user, with a clip to attach to the user's pocket or belt. U.S. Pat. No. 5,892,233 ("the '233 patent"), which issued to Richard T. Clement on Apr. 6, 1999, is an example that describes such techniques.

The device disclosed in the '233 patent and the like suffer certain problems by virtue of the structure and materials employed. For example, the device depicted therein requires a component to uphold the medical apparatus such as stethoscope, thereby entailing unnecessary parts and materials. Moreover, the materials used for the disclosed device such as clear plastic and glass do not provide effective irradiation due to their transparency quality.

SUMMARY OF THE INVENTION

Given the above deficiencies of prior art, there is a need for a disinfecting and sterilizing device that effectively and efficiently uses UV light to sterilize various objects such as medical or lavatory devices.

The sterilizing device in accordance with the present invention includes a closed housing, a power supply, a switch, and ultraviolet (UV) lamps. Preferably, the UV lamps are mounted on walls of the housing. The switch is controlled to set on and off the UV lamps. The switch can be configured to turn off the power supply automatically after a predetermined period of time.

Advantageously, the sterilizing device includes a stethoscope. The closed housing covers the stethoscope head that comes in contact with the human or animal subject. It is preferably used with a holster for receiving the stethoscope.

The UV lamp used in the inventive device preferably generates radiation with a wavelength ranging from 200 nm to 290 nm. Radiation with a 254 nm wavelength generally has the optimal germicidal effect.

According to one embodiment of the present invention, the power supply includes a re-chargeable battery.

Advantageously, the sterilizing device is constructed of reflective materials, or, comprises walls with reflective materials on their surfaces, so as to maximize the irradiation rate of the UV light.

For users' convenience, a tray is included for placing the object to be sterilized. In addition, a wall mount mechanism may be added to mount the sterilizing device on a fixture.

DETAILED DESCRIPTION OF THE INVENTION

Figure 1A:
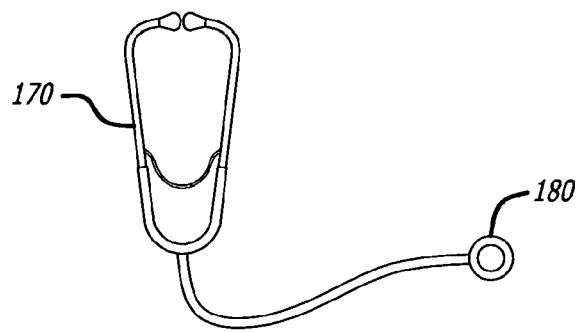
FIG. 1 illustrates an exemplary embodiment of the sterilizing device having an opening configured to receive the head of a stethoscope.
Figure 1B:
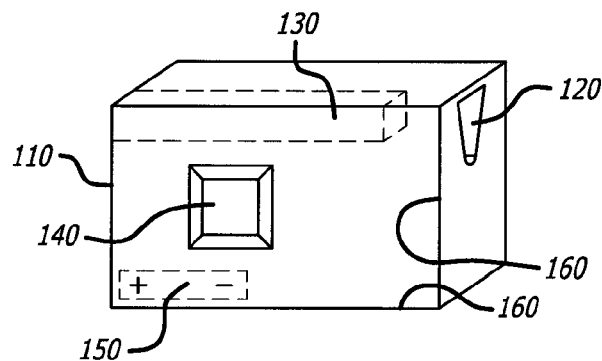
Figure 1B:
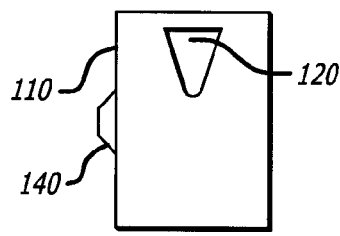
Figure 1C:
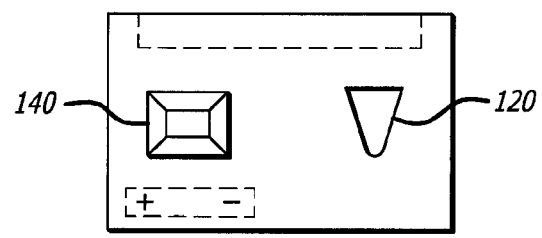

FIG. 1A shows an exemplary embodiment of the UltraViolet (UV) light sterilizing device of the present invention along with a standard stethoscope 170. The sterilizing device comprises a housing 110, opening 120, UV light source 130, control switch 140, object sensor 145, power supply 150, and reflective inner surfaces 160. The stethoscope 170 comprises a diaphragm or bell-containing head 180 that is placed in contact with the human or animal subject in order to provide medical diagnosis. While the description below references a stethoscope head as the object that is sterilized by the device, other objects can be sterilized in accordance with the device of the present invention. FIG. 1B shows a side view of the device facing the opening 120. Alternatively, as shown in FIG. 1C, the opening 120 and control switch 140 can be on the same surface of the device. The housing 110 is a hollow, rectangular body, although other suitable shapes could be used in accordance with the invention. The housing 110 should be compact enough to allow for convenient use and storage, while being large enough to house the UV light source 130, power supply 150, and object to be sterilized. The relative positioning and dimensions of the device and its parts shown in the Figures is not intended to be to scale, but rather, the Figures are designed for ease of reference. In an exemplary embodiment, UV light source 130 can be a hot cathode UVC lamp with the following specifications: length of 63 mm, GTL3, lamp wattage 3, tube diameter 20 mm, base E17, total watts 0.18, 1.8 microwatts per square cm at 1 meter, average lamp life 2,000 hours, emitting 253.7 nm wavelength UVC light. UV light has been shown to have its optimal germicidal affect at a wavelength of 254 nm.

An object sensor 145 is positioned inside the housing 110 such that placing an object into the opening 120 triggers the object sensor 145 and activates the UV light source 130. In an exemplary embodiment, the object sensor 145 can be a button or switch that is physically moved or depressed when the object to be sterilized is placed in opening 120. Placing the object in the opening 120 changes object sensor 145 from its resting position to an activated position. For example, object sensor 145 can be a normally-off, push-button switch that is activated when the object is placed in the opening. Other sensing means known in the art, such as infrared sensors, could also be employed. When object sensor 145 detects the presence of an object, the UV light source 130 is turned on (i.e. activated) and the object is thereby sterilized by exposure to the UV light. In an exemplary embodiment, activation of the UV light source results in 5 second pulses of light being delivered for a duration of 60 seconds, although the manner and duration of UV light exposure can be varied while staying within the scope of the invention. Additionally, the UV light source 130 can be manually controlled using control switch 140, whereby pressing the control switch provides a UV light pulsing sequence (e.g. 5 second pulses of UVC light for a duration of 60 seconds). The inner surfaces of the housing 110 are covered with a light-reflective material so that the UV light exposure is more uniformly and intensely distributed throughout the housing in order to provide more effective sterilization of the stethoscope head 180.

Thus, a medical worker can place the stethoscope head 180 into the opening 120 and sterilization will begin automatically without the need for additional manual contact. Alternatively, the device can include a mode selection button whereby the user can deactivate the object sensor 145 in favor of purely manual control of the UV light exposure, based on preference. However, minimizing the user's contact with the device provides a more sterile environment so automatic sterilization utilizing the object sensor 145 is preferred. However, in some situations, the user may want to re-sterilize the object, such as when the object has been resting idle in the opening 120 for an extended period of time, or if additional UV exposure is desired. The user could re-activate the object sensor 145 and re-sterilize the object by removing the object and putting it back in the opening 120. However, in order to minimize contact with the device, control switch 140 allows the user to re-sterilize the object with touching it.

Existing UVC anti-microbial wands use a power supply of four AA batteries totaling 6 volts (1.5 volts/alkaline battery). In an exemplary embodiment, and in order to minimize size and weight, the device of the present invention utilizes a power supply 150 that consists of a single 6 volt battery (e.g. Duracell 28A) or four silver batteries (e.g. Duracell 76S). However, other suitable and more advanced power supplies may be used as known in the art. The power supply 150 may be provided by standard or rechargeable batteries. The opening 120 is optimally configured to allow the diaphragm or head 180 of stethoscope 170 to be easily inserted into the housing 110, while providing maximum shielding and protection from the external environment during UV light exposure. Opening 120 holds the head 180 (or other object) in place during UV light exposure, or when otherwise desired to keep the head 180 secure and protected. The device thus allows for medical staff to disinfect a stethoscope diaphragm or other suitable object without the need for clean water and alternate sterilization methods.

The device of the present invention may be stored and used from a counter top, or alternatively, it may be mounted on a wall. In a preferred wall-mounted embodiment, the device allows for convenient storage of the stethoscope or other medical device with minimal manual interaction.

Figure 2A:
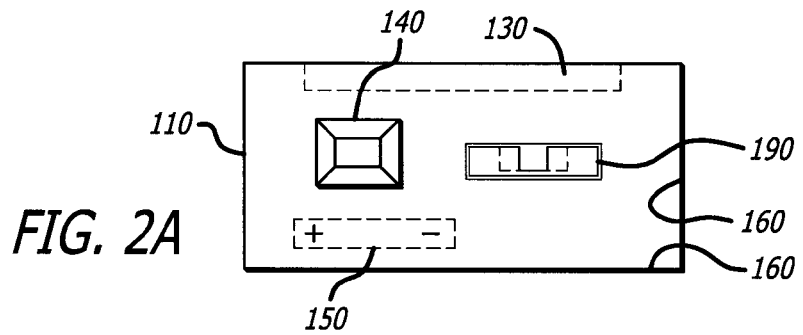
FIG. 2 illustrates an exemplary embodiment of the sterilizing device having a retractable sliding tray configured to receive the head of a stethoscope or other medical device.

In an alternate embodiment shown in FIG. 2, the device includes a retractable tray 190 that is configured to receive the head 180 and then pull it into the housing 110 for UV light exposure. The retractable tray 190 allows the inside of the housing to be further isolated from the environment and free from contaminants, because there is no longer a permanent opening 120 (see FIG. 1) in the device. When the tray is in the closed or retracted position, the device is essentially sealed and the housing is free from particulate matter and contaminants that may enter from the environment. This allows a user to place the stethoscope onto the tray, without handling the device. Once the stethoscope is placed on the tray, it is automatically pulled into the housing 110 using an opening and closing mechanism as known in the art (e.g. CD/DVD players). The retractable tray can be operated by a button or the tray itself may be touch-activated as known in the art (e.g. spring-activated panel). The user can then wash their hands and perform other tasks while the stethoscope or other medical device is being sterilized. Aside from sterilization, the device provides a clean and convenient place to store the stethoscope while it's not in use.

Figure 2B:
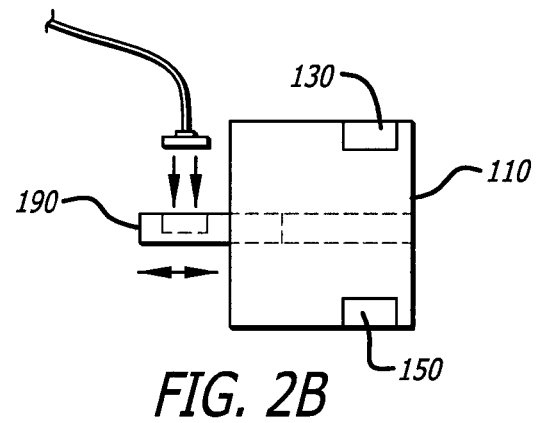
Figure 2C:
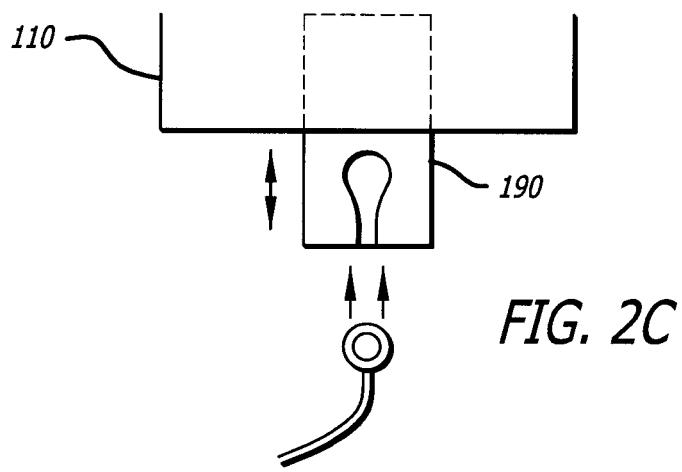
Figure 3A:
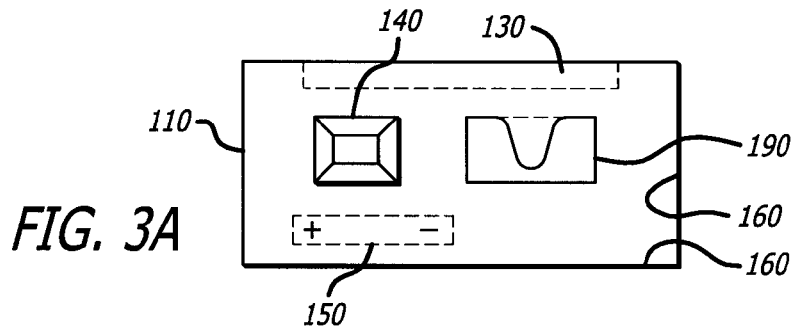
FIG. 3 illustrates an exemplary embodiment of the sterilizing device having a retractable hinged tray configured to receive the head of a stethoscope or other medical device.
Figure 3B:
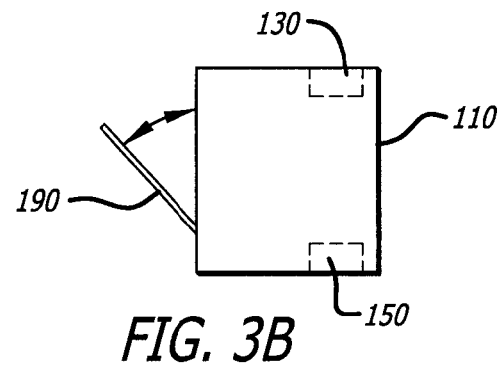
Figure 3C:
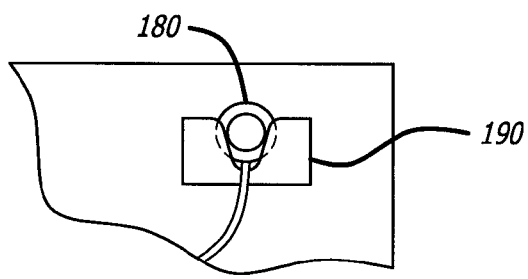

FIGS. 2B and 2C are side and top views of the device, respectively, that show the retractable tray extended outside the housing 110. This embodiment is ideally mounted on a wall for optimal convenience. FIG. 3 shows an alternate embodiment of the retractable tray, which comprises as a hinged door, rather than a sliding tray. Like a draw-bridge, the hinged tray is hinged at its bottom edge and is free at its top edge. The hinged tray rotates about the bottom hinged edge and the top edge of the tray opens at an angle from the vertical axis. As with the sliding tray, the hinged tray can operate via a mechanism known in the art and can be activated by either a button on the device or by touching the tray itself (i.e. touch-activated panel). Both the retractable tray embodiments provide a more sanitary device by keeping the inside of the housing cleaner and protecting the stethoscope head (or other object) from external contaminants during UV exposure.

Figure 4:
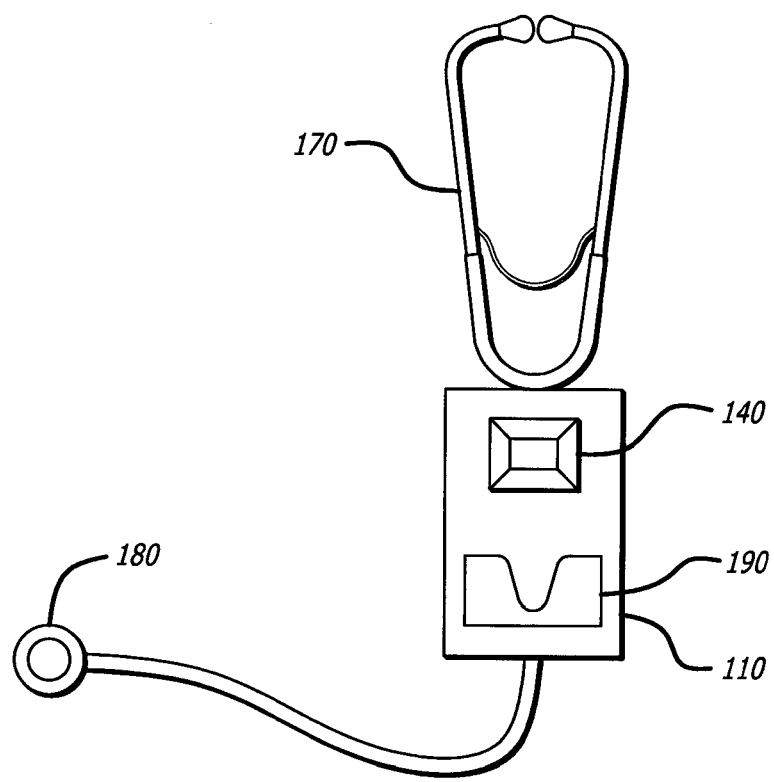
FIG. 4 illustrates an exemplary, portable embodiment of the sterilizing device in accordance with the present invention.

In another embodiment shown in FIG. 4, the device can be configured to be worn by the medical worker by attaching to the center of the stethoscope near the user's chest or on the belt as a holster. This device is portable and can utilize batteries (standard or rechargeable) and is therefore not limited by cables and the need for connection to a power outlet. A simple attachment means on the back of the device (e.g. hook or straps) can be used to attach the device to the stethoscope worn by the medical worker or to the user's belt. Whenever the user wants to sterilize the stethoscope, they place the head 180 into the retractable tray or opening, which activates the UV light exposure sequence. The head-receiving means can be a static opening as shown in FIG. 1 or a retractable tray as shown in FIG. 2 or 3. The embodiment of a retractable tray 190 is shown in FIG. 3. Thus, this embodiment allows the user to sterilize the stethoscope head wherever they go and also provides a holder that protects the head 180 during times of non-use.

As advancements in technology allow the UV light source and power supply to be reduced in size, the device of the present invention can be reduced in size such that it can fit in the palm of the hand and act as a removable sterilizing cover for the stethoscope head. Thus, in this "sterilizing cover" embodiment, the device size is only limited by the size of the stethoscope head (or other object to be sterilized) rather than the UV lamp and power source size, such that the housing 110 is more akin to a sleeve or cover.

While there have been described herein what are considered to be preferred and exemplary embodiments of the present invention, other modifications of the invention shall be on apparent to those skilled in the art from the teachings herein. The particular dimensions of the device and its components shown or described herein, as well as variations in materials, shapes, relative sizes, assembly and use, should be readily understood by one of ordinary skill in the art. It is therefore desired to be secured, in the appended claims all such modifications as fall within the spirit and scope of the invention.

What is claimed is:

1. A device employing UV light for sterilizing, comprising:
    a closed housing with an opening configured to receive an object to be sterilized;
    a power supply;
    a control switch;
    an object sensor; and
    at least one ultraviolet light source mounted within the housing, wherein the ultraviolet light source is controlled by the control switch and the object sensor; wherein
    the housing contains a reflective material on a plurality of its inner surfaces; and wherein
    all surfaces of the object are irradiated by ultraviolet light.

2. The device of claim 1, wherein the opening is configured to receive the head of a stethoscope.

3. The device of claim 1, wherein the object sensor is configured to sense the presence of an object that is placed in the opening and thereby activate the at least one ultraviolet light source.

4. The device of claim 1, wherein the object sensor is an infrared sensor.

5. The device of claim 1, wherein the object sensor is a normally-off, push-button switch that is activated upon placement of the object in the opening.

6. The device of claim 1, further comprising a fastener configured to fasten the device to the user's clothing.

7. The device of claim 1, wherein the UV lamp generates radiation with a wavelength ranging from 200 nm to 290 nm.

8. The device of claim 1, wherein the UV lamp generates radiation with a wavelength of 254 nm.

9. The device of claim 1, wherein the power supply is a re-chargeable battery.

10. The device of claim 1, further comprising a mechanism for mounting the device on a vertical wall and/or desktop.

11. A device employing UV light for sterilizing, comprising:
    a closed housing;
    a retractable tray that extends from the housing, the tray configured to receive an object to be sterilized;
    a power supply;
    an object sensor;
    a switch; and
    at least one ultraviolet light source mounted within the housing, wherein the ultraviolet light source is controlled by the control switch and the object sensor; wherein
    the housing contains a reflective material on a plurality of its inner surfaces; and wherein
    all surfaces of the object are irradiated by ultraviolet light.

12. The device of claim 11 wherein the retractable tray is configured to slide horizontally in and out of the housing.

13. The device of claim 11 wherein the retractable tray is hinged at a bottom end and free at a top end, wherein the tray opens at an angle from the vertical axis.

* * * * *